United States Patent [19]

Müller

[11] Patent Number: 4,792,337
[45] Date of Patent: Dec. 20, 1988

[54] ACETABULUM PART FOR A TOTAL HIP PROSTHESIS

[75] Inventor: Maurice E. Müller, Bern, Switzerland

[73] Assignee: Protek AG, Bern, Switzerland

[21] Appl. No.: 104,953

[22] Filed: Oct. 6, 1987

[30] Foreign Application Priority Data

Oct. 16, 1986 [CH] Switzerland ............... 04141/86
Nov. 7, 1986 [CH] Switzerland ............... 04467/86

[51] Int. Cl.$^4$ .................................. A61F 2/32
[52] U.S. Cl. ............................................. 623/22
[58] Field of Search .............................. 623/16-23

[56] References Cited

U.S. PATENT DOCUMENTS

| 3,608,096 | 6/1971 | Link | 3/1 |
|---|---|---|---|
| 3,840,904 | 10/1974 | Tronzo | 623/22 |
| 3,903,549 | 3/1975 | Deyerle | 311/912 |
| 4,662,891 | 5/1987 | Noiles | 623/22 |
| 4,695,282 | 9/1987 | Forte et al. | 623/22 |

FOREIGN PATENT DOCUMENTS

| 2314708 | 10/1974 | Fed. Rep. of Germany | 623/22 |
|---|---|---|---|
| 2822585 | 11/1979 | Fed. Rep. of Germany | 623/22 |
| 3310944.3 | 10/1984 | Fed. Rep. of Germany | 623/22 |
| 0142759 | 5/1985 | Fed. Rep. of Germany | 623/23 |
| 0091315 | 10/1983 | United Kingdom | 623/22 |
| 2139098 | 11/1984 | United Kingdom | 623/18 |

OTHER PUBLICATIONS

Schneider, Robert; "Aktuelle Probleme in Chirurgie und Orthopädie", 1982, pp. 30–33.
"The Journal of Bone and Joint Surgery", 68-A, Apr. 1986, p. 91.
"The Journal of Bone and Joint Surgery", 68-B, May 1986, p. ii.
"The Year Book of Orthopedics", Chapter 3, p. 175.
Copy of photographs of model as submitted to the Swiss Patent Office, No. 110826.
Copy of photographs of model as submitted to the Swiss Patent Office, No. 110827.

Primary Examiner—Richard J. Apley
Assistant Examiner—David J. Isabella
Attorney, Agent, or Firm—Walter C. Farley

[57] ABSTRACT

An acetabulum part for a total hip prosthesis has a metallic anchoring shell (1) whose convex surface facing the pelvic bone essentially has the form of a spherical cap, with a socket insert (2) that can be inserted into the anchoring shell (1) whose external convex form is adjusted to the interior concave form of the anchoring shell (1) in such a way that it can be fixed against rotation without using bone cement in the anchoring shell (1). The internal concave form of the insert (2) allows for friction-free and undisturbed motion of a synthetic femur ball head. The shell (1) has several slits (9) located along the meridians of the spherical cap and has numerous holes (6) between the equatorial line and the pole of the spherical cap for the cement-free primary anchoring in the pelvic bone with anchoring screws (3).

24 Claims, 3 Drawing Sheets

ACETABULUM PART FOR A TOTAL HIP PROSTHESIS

This invention relates to an acetabulum part total hip prosthesis, comprising a metallic anchoring shell whose convex surface facing the pelvis essentially has the form of a semi-spherical cap, with holes for cementless primary anchoring in the pelvis by means of anchoring screws and a socket insert that can be implanted in the anchoring shell wherein the external convex form of the socket insert is adapted to the internal concave form of the anchoring shell so that it an be fixed in the anchoring shell and secured against rotation without the use of bone cement and its internal concave form allows for friction-free and undisturbed movement of a synthetic femur head in an essentially known fashion.

BACKGROUND OF THE INVENTION

Joint sockets to be used as counterbearings or support bearings for the synthetic femur head are preferably made of highly polymerized polyethylene. These synthetic sockets are often implanted directly into the acetabulum which has been ground down accordingly. But based on leading opinion today, a bone-metal-polyethylene configuration is preferred over the bone-polyethylene configuration, as presented, for example, by Mark B. Coventry in the Year Book of Orthopedics, Chicago, Year Book Medical Publishers Inc., 1985, p. 175.

In order to realize the synthetic hip socket in the bone-metal-polyethylene configuration preferred today, a threaded metal ring is known, e.g. from European patent application No. 0142759 which is inserted into the acetabulum and into which a polyethylene socket is clamped.

Polyethylene hip joint sockets are also known whose rim is partially extended i.e. has a partially raised shoulder, in order to reduce the danger of slippage of the synthetic femur head from the socket, that is to reduce the danger of dislocation. Such joint sockets, e.g., are known as "poly-dial inserts" of the Joint Medical Products Corporation, advertisement in "The Journal of Bone and Joint Surgery", 68-A, April 1986, p. 91, or of polyethylene inserts of the Waldemar Link GmbH & Co., advertisement in "The Journal of Bone and Joint Surgery", British Volume 680B, May 1986, following p ii.

In order to be able to install a socket prosthesis even under unfavorable circumstances with the pelvis, such as in the case of bone defects, a larger support surface has to be created between the metal ring and the pelvis. For this purpose, German patent No. 2314708 calls for a metal shell with a support flange which is anchored in the acetabulum with bone cement and in which the polyethylene socket is inserted, similarly with the help of bone cement.

In order to achieve reliable power transfer from the prosthesis to the pelvis despite reduced or weakened bone substance, socket cover shells made of metal, as presented by M. E. Mueller, or socket support shells, as presented by H. B. Burch and R. Schneider, are used. See, e.g., R. Schneider, "Total Prosthesis of the Hip", Bern, Hans Huber Publishers, 1982, p. 30 ff. The socket cover shell based on M. E. Mueller and the socket support shell based on H. B. Burch and R. Schneider are also known from the entry as the Swiss sample and model Nos. 110.826 and 110.827, respectively.

These socket cover shells or socket support shells are anchored in the bone, primarily with screws. The polyethylene socket is secured in the metal shell by means of bone cement. As a result, the bone cement also penetrates the holes of the metal shell and contributes to the mounting of the metal shell in the bone.

In order to secure the acetabulum part of a hip prosthesis in the pelvis without using bone cement, P. Schuster in Swiss patent application No. 3252/84-9 proposed a metal shell with a pole area that is essentially parallel to the equator of the sphere and which has knife-like edges that are distributed evenly across the periphery of the sphere. The external shape has the form of an octagon at the equator level such that there is the possibility for primary fixation in the pelvic bone by means of screws.

SUMMARY OF THE INVENTION

An object of the present invention is to create an acetabulum part of a hip prosthesis which has a metal shell for anchorage into the pelvic bone without using bone cement and also has a socket insert that is implanted into this metal shell, similarly without cement, that is made of a suitable material such as polyethylene, metal or ceramics, such that slippage or rotation of the metal anchoring shell in the pelvic bone is prevented by means of its structural arrangement.

Briefly described, the invention comprises an acetabulum part for a total hip prosthesis having a metallic anchoring shell in the shape of a cap having a rim, a substantially spherical convex outer surface and means defining a plurality of slits through the shell, the slits being elongated along longitudes of a sphere conforming to the spherical surface. A plurality of holes are located between an equatorial line about the spherical surface and the pole of the spherical surface. A plurality of anchoring screws are shaped and dimensioned to pass outwardly through the holes and into the pelvis for adhesive-free primary anchoring of the shell in the pelvic bone. A socket insert has an exterior surface shaped to conform to the interior surface of the shell so that the socket is non-rotatably received in the shell in the absence of an adhesive and an interior surface shaped to receive a synthetic femur head for substantially friction-free, undisturbed movement of the femur head therein.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this invention, and wherein.

DESCRIPTION OF THE PREFERRED EMBODIMENTS

Figure 1:
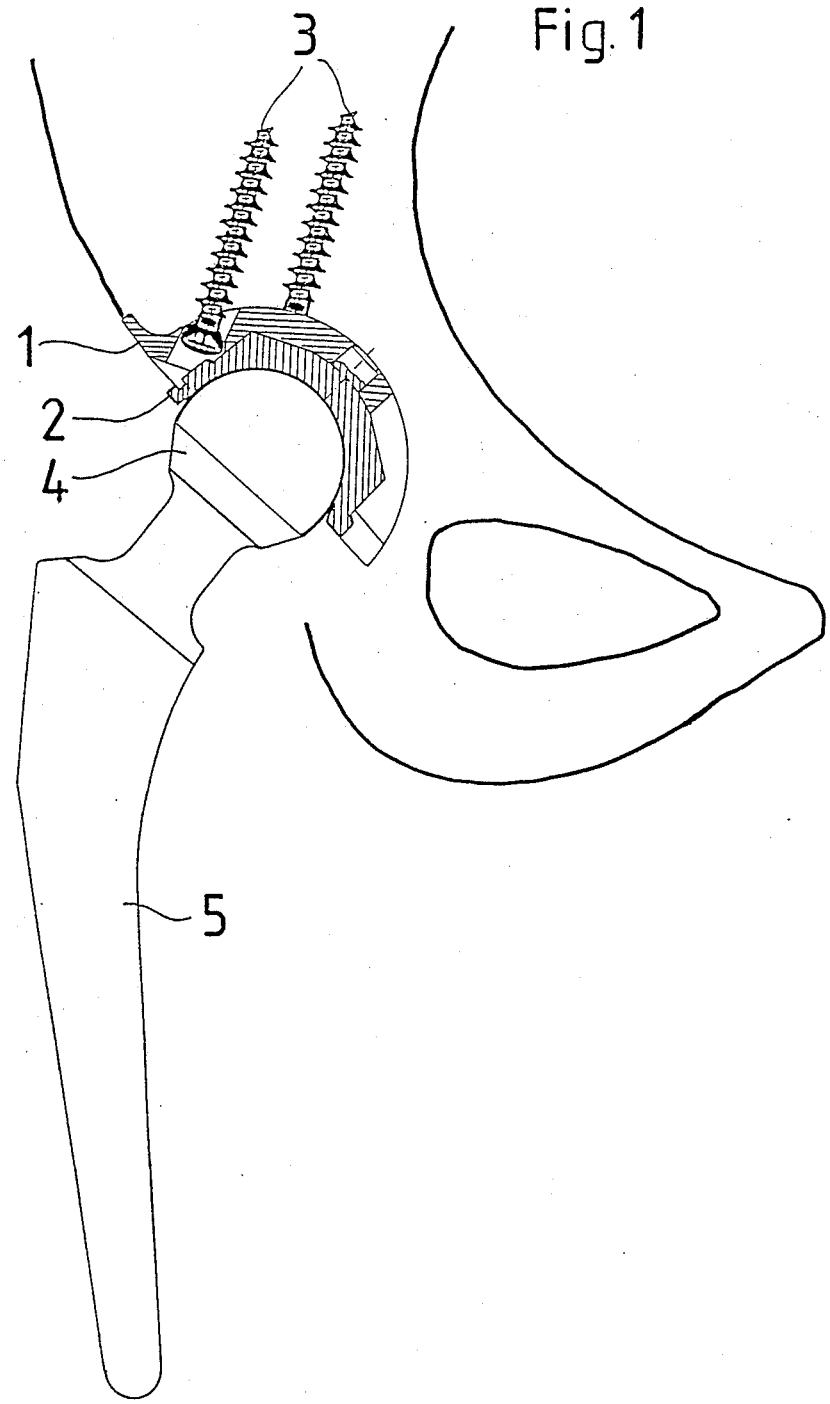
FIG. 1 is a schematic side elevation in partial section of a complete synthetic hip joint.

FIG. 1 is the front view of the right side of the human pelvis with an anchoring shell 1 secured therein, a socket 2 which is made of plastic or of another suitable material (e.g. metal, ceramic-coated metal, ceramic or a composite material), anchoring screws 3, a synthetic femur head 4, and a femur prosthesis 5.

Figure 3:
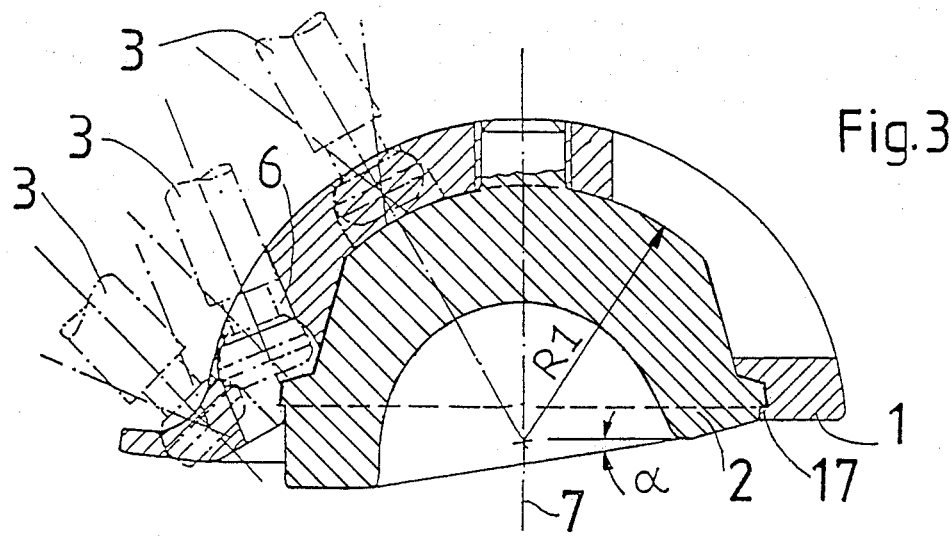
FIG. 3 is a side elevation of the structure of FIG. 1.

FIG. 3 shows a cross-sectional view of a preferred embodiment of the anchoring shell 1, with holes 6 for the anchoring screws 3, the socket 2 and the rotational axis 7, with respect to the cone 13.

Figure 2:
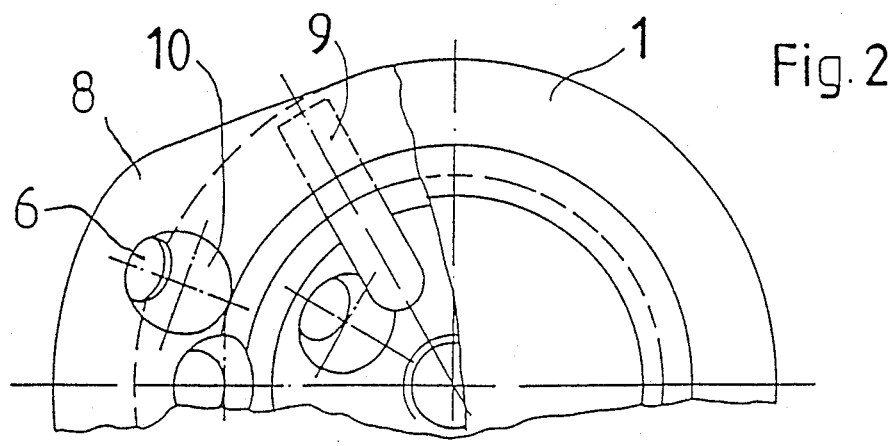
FIG. 2 is a partial bottom plan view of an anchoring shell in accordance with the invention with a partially cutaway socket insert in an embodiment that is preferred for a socket insert made of plastic.
Figure 4:
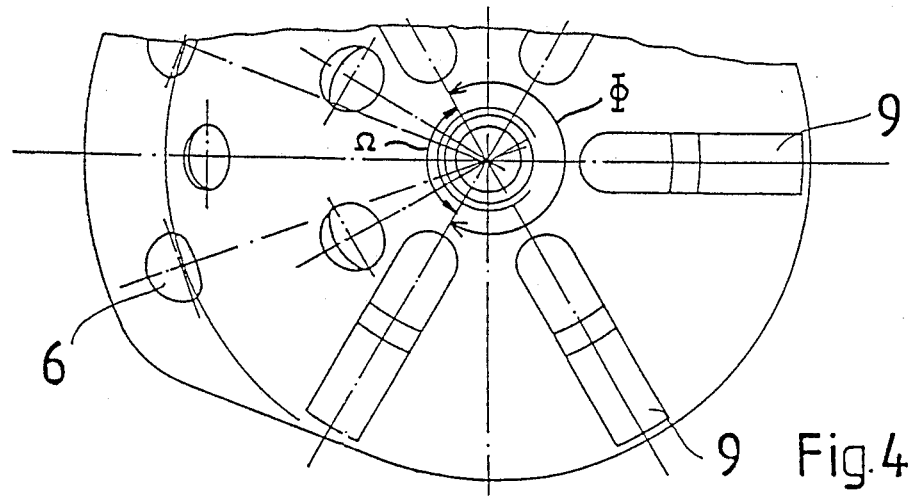
FIG. 4 is a top plan view of the structure of FIGS. 2 and 3 of the anchoring shell in an embodiment that is preferred for socket inserts made of plastic.
Figure 5:
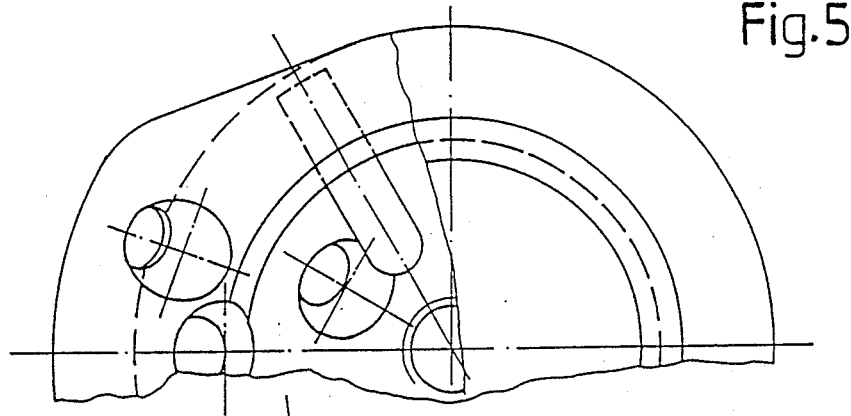
FIGS. 5 and 7 are top and bottom plan views, respectively, of the structure of FIG. 6.
Figure 6:
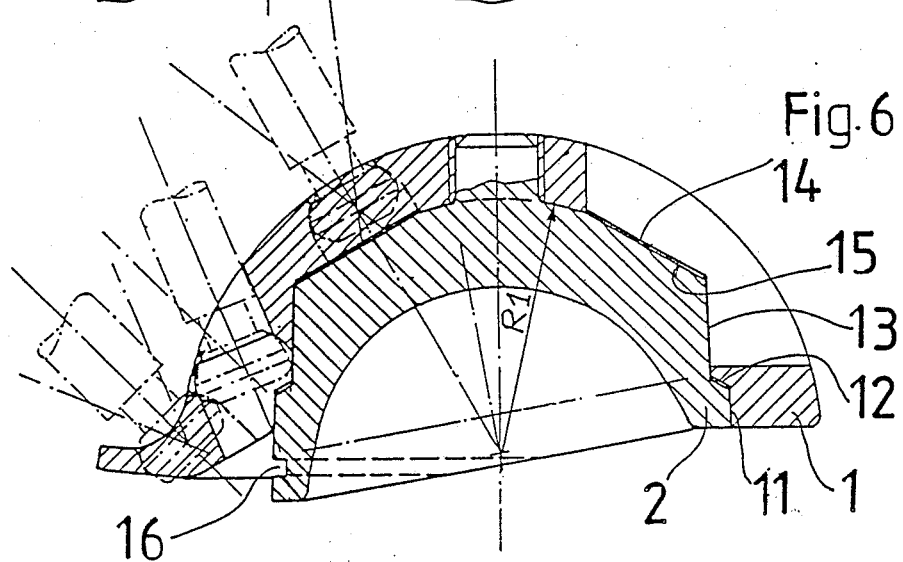
FIG. 6 is a side elevation in section of the anchoring shell and the socket insert in accordance with the invention in a preferred embodiment for socket inserts made of metal.
Figure 7:
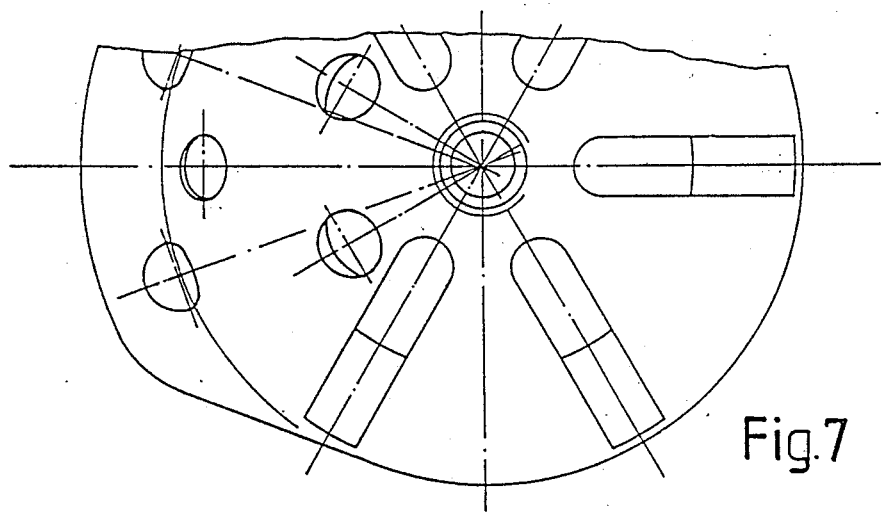

FIGS. 2 and 4 show top and bottom plan views of a preferred embodiment of the anchoring shell 1 having a collar 8 which extends over an angle of between about 70° and about 140° from the rim of the near-hemisphere to enlarge the bone-contact area. These figures also show slits or through slots 9 and the holes 6, for receiving the anchoring screws 3. The through-slots 9 have a width in the direction of latitudes of the sphere of between about 3 mm and about 7 mm, all of them being of about equal width. The through-slots are distributed over about 210° to about 270°, the remaining area being devoted to holes 6. Within their sector, the through-slots are substantially uniformly spaced. The through-slots can extend from a latitude circle of diameter 12 mm to a point about 5 mm from the rim. Holes 6 have enlarged inner cavities 10 for receiving the enlarged heads of the screws.

The anchoring shell 1 is preferably manufactured of pure titanium. The structure in accordance with the invention is suitable for socket inserts 2 made of different materials such as polyethylene, ceramics or metal. Individual structural features are different, however, depending upon whether a socket insert 2 made of plastic or another material with a high elasticity modulus, such as metal or ceramics, is used.

The essential structural features are described with reference to FIGS. 2, 3 and 4 in which the preferred embodiment for a socket insert 2 made of polyethylene is depicted.

The protrusion 17 of the socket insert made of plastic snaps into a corresponding groove of the anchoring shell 1 in order to prevent displacement of the socket insert 2 during the operation while the femur ball head is being embedded. The femur ball head then presses the socket insert 2 against the spherical surface with its radius, R1, and the surrounding conical surface 13.

The undesired twisting of the socket insert 2 with respect to the anchoring shell 1 can be reliably prevented by the fact that the socket insert 2 is designed with protrusions or elevations (not shown in diagram 3) which are shaped and dimensioned to fit into the slits 9.

In order to reduce the risk of dislocation, the rim of the socket insert 2 is designed in such a way that it is not on a plane that is perpendicular to the rotational axis 7 of the cone, but rather is on a plane which deviates by the angle α from 90° as seen in FIG. 3. For this purpose, α = 10° is preferred.

Another improvement in the acetabulum part presented by the invention consists of the structural design of the holes 6 for the anchoring screws 3, the enlarged inner parts 10 being ellipsoidal-shaped to receive the heads so that the surgeon can screw in the screws 3, which are standard for orthopedic surgery, at the biomechanically optimal angle which deviates between about 20° to about 30° from the axis of the hole without the screw head hindering the insertion and clamping of the socket insert 2 and without the wall of the anchoring shell 1 having to be made undesirably thick.

The acetabulum part shown in diagrams 5, 6 and 7, which is a preferred embodiment for a socket insert 2 made of metal, has an additional conic surface 14 on the concave interior of the anchoring shell 1 and an additional conic surface 15 on the convex external side of the socket insert, and only the parts of the anchoring shell 1 and the socket insert 2 near the pole have a spherical shape.

The socket insert 2, made of metal, clamps in at the conic surface 13 when pressure is applied, and is rotation-free.

The implantation of the acetabulum part of the hip prosthesis in accordance with the invention occurs in the following way: Once the acetabulum has been filed down, the anchoring shell 1 is secured in the position best suited for force transfer with the aid of three to five screws 3.

The through-slots 9 allow for controlling good contact of the anchoring shell 1 with the bone.

Bone material obtained from the filed femur head or other bone material can be inserted, if necessary, through the through-slots 9 into the area between the filed acetabulum and the anchoring shell 1.

Then the socket insert 2 is inserted into the anchoring shell 1 in such a way that the vector of the resulting force exerted by the femur head on the socket is close to the through-slots level which can be established by the rotational axis 7 and the highest point of the rim 2 of the socket insert.

The bone that grows into the through-slots 9 of the anchoring shell 1 following implantation of the acetabulum part supports the stable anchoring and especially increases the reliability against undesired rotation of the anchoring shell 1.

The through-slots 9 are situated, as shown in FIG. 4, along the meridians with an angular range, Φ, of 240° of the spherical longitude of the spherical cap separated by substantially equal angles. The holes 6 are situated in the remaining through-slots free angle range $\Omega = 360° - \Phi$ of the longitude of the spherical cap.

The essential advantages of the combined configuration of through-slots 9 and holes 6 based on the invention are found in the fact that adequate primary fixation is achieved directly after the implantation of the acetabulum part whereas securement against rotation is primarily achieved by the possibility of inserting bone-like material into the area of the through-slots 9.

What is claimed is:

1. An acetabulum part for a total hip prosthesis comprising the combination of
    a metallic anchoring shell in the shape of a cap having a rim, a substantially spherical convex outer surface facing the pelvic bone and a concave interior surface;
    means defining a plurality of slots passing through said shell, said through-slots being elongated along longitudes of a sphere conforming to said spherical surface and said through-slots being dimensioned to provide sufficient area for the introduction and implantation of bone graft material therein.
    means defining a plurality of holes located between an equatorial line about said spherical surface and the pole of said spherical surface;

a plurality of anchoring screws shaped and dimensioned to pass outwardly through said holes and into the pelvis for adhesive-free primary anchoring of said shell in the pelvic bone; and a socket insert having an exterior surface shaped to conform to the interior surface of said shell so that said socket is non-rotatably received in said shell in the absence of an adhesive and an interior surface shaped to receive a synthetic femur head for substantially friction-free, undisturbed movement of said femur head therein.

2. An acetabulum part according to claim 1 wherein said through-slots have a width in the direction perpendicular to said longitudes which is between about 3 mm and about 7 mm.

3. An acetabulum part in accordance with claim 2 wherein all of said through-slots are of the same width.

4. An acetabulum part in accordance with claim 3 wherein each of said through-slots has at least one semicircular end.

5. An acetabulum part in accordance with claim 4 wherein said through-slots are located along longitudes and extend over an angle of between about 210° and about 270° as measured along a latitudinal line, said through-slots being substantially uniformly angularly spaced.

6. An acetabulum part in accordance with claim 5 wherein the beginning of said through-slots closest to the pole of said spherical cap lies on a latitude of said cap having a diameter of at least 12 mm and said through-slots extend at the most to a distance of about 5 mm from the rim of said shell.

7. An acetabulum part in accordance with claim 6 wherein said socket insert includes means on the outer surface thereof forming protrusions and positioned to extend into said through-slots in said shell.

8. An acetabulum part in accordance with claim 1 wherein said shell further comprises a laterally extending flange protruding laterally outwardly from the lower rim thereof and extending over an angle of between about 70° and about 140° along said rim for enlarging the contact surface between said shell and the pelvic bone.

9. An acetabulum part in accordance with claim 8 wherein said holes are located only in the area of said cap not occupied by said through-slots.

10. An acetabulum part in accordance with claim 9 wherein each of said anchoring screws has an enlarged head for engaging said shell and each of said holes is formed with an enlarged cavity adjacent the interior surface of said shell to receive the heads of said anchoring screws so that said heads do not protrude inwardly beyond said interior surface.

11. An acetabulum part in accordance with claim 10 wherein each said enlarged cavity is shaped to receive said heads such that each said anchoring screw extends into the pelvic bone at an angle which is separated from the central axis of the associated hole by between about 20° and about 30°.

12. An acetabulum part in accordance with claim 11 wherein each said enlarged cavity has the shape of a part of an ellipsoid.

13. An acetabulum part in accordance with claim 12 wherein said insert is formed with a protrusion on the outer surface thereof and said shell is formed with a corresponding recess to receive said protrusion to limit relative motion therebetween.

14. An acetabulum part in accordance with claim 13 wherein the exterior surface of said shell is formed with a smooth, gradual transition between said spherical surface and said flange.

15. An acetabulum part in accordance with claim 14 wherein said outer surface of said shell is formed with a flattened portion at the pole thereof.

16. An acetabulum part in accordance with claim 15 wherein said interior surface of said shell includes a spherical portion around said pole and a conical portion adjacent said rim.

17. An acetabulum part in accordance with claim 15 wherein said interior surface of said shell and the exterior of said insert are formed with a series of conical surfaces and said insert and said shell are shaped and dimensioned so that said insert nonrotatably engages said conical surfaces.

18. An acetabulum part in accordance with claim 17 wherein one of said conical surfaces on the exterior of said insert is formed with a groove.

19. An acetabulum part in accordance with claim 17 wherein the rotational axis of said conical surfaces of the interior of said shell is the same as the axis of said spherical outer surface.

20. An acetabulum part in accordance with claim 19 wherein the outer pelvis-oriented convex form of the rotationally symmetrical part of said socket insert is an image of the rotationally symmetrical part of the internal concave surface of said shell except for said through-slots and wherein said shell and insert are shaped and dimensioned so that said insert is secured against rotation relative to said shell.

21. An acetabulum part in accordance with claim 20 wherein each of said shell and insert has a rim substantially lying in a plane and wherein the plane containing said rim of said insert deviates from a 90° relationship with said central rotational axis of said shell.

22. An acetabulum part in accordance with claim 21 where said angle deviating from a 90° relationship with said central axis is less than 90° and greater than 80°.

23. An acetabulum part for a total hip prosthesis comprising the combination of a metallic anchoring shell in the shape of a cap having a rim, a substantially spherical convex outer surface facing the pelvic bone and a concave interior surface;

means defining a plurality of through-slots of substantially equal width through said shell extending over an angle of between about 210° and 270° as measured along a latitudinal line, said through-slots being substantially uniformly angularly spaced, each of said through-slots being elongated along a longitude of a sphere conforming to said spherical surface, each of said through-slots having a semicircular end and said through-slots being dimensioned to provide sufficient area for the introduction and implantation of bone graft material therein.

means defining a plurality of holes located only in areas not occupied by said through-slots between an equatorial line about said spherical surface and the pole of said spherical surface, each of said holes having an elongated cavity in the shape of a portion of an ellipsoid adjacent the interior surface of said shell to receive an enlarged head of an anchoring screw so that said head does not protrude inwardly beyond said interior surface, each said cavity being shaped to receive a head so that the screw extends into the pelvic bone at an angle which diverges from the central axis of the associated hole by between about 20° and about 30°;

a plurality of anchoring screws shaped and dimensioned to pass outwardly through said holes and into the pelvis, each of said anchoring screws having an enlarged head for engaging said shell for adhesive-free primary anchoring of said shell in the pelvic bone; and a plurality of socket inserts each having an exterior surface shaped to conform to the interior surface of said shell so that said socket is non-rotatably receivable in said shell in the absence of an adhesive, each of said inserts having an interior surface shaped and dimensioned to receive one of a plurality of synthetic femur heads of different sizes for substantially friction-free, undisturbed movement of said one of said femur heads therein.

24. An acetabulum part for a total hip prosthesis comprising the combination of a metallic anchoring shell in the shape of a cap having a rim, a substantially spherical convex outer surface facing the pelvic bone and a concave interior surface;

means defining a plurality of through-slots through said shell, said through-slots being elongated along longitudes of a sphere conforming to said spherical surface and said through-slots being dimensioned to provide sufficient area for the introduction and implantation of bone graft material therein;

means defining a plurality of holes located between an equatorial line about said spherical surface and the pole of said spherical surface;

a plurality of anchoring screws shaped and dimensioned to pass outwardly through said holes and into the pelvis for adhesive-free primary anchoring of said shell in the pelvic bone; and a plurality of socket inserts each having an exterior surface shaped to conform to the interior surface of said shell so that each said socket is non-rotatably receivable in said shell in the absence of an adhesive, each of said inserts having an interior surface shaped and dimensioned to receive one of a plurality of synthetic femur heads of different sizes for substantially friction-free, undisturbed movement of said one of said femur heads therein.

* * * * *